US006179841B1

(12) United States Patent
Jackson

(10) Patent No.: US 6,179,841 B1
(45) Date of Patent: *Jan. 30, 2001

(54) SET SCREW FOR USE WITH OSTEOSYNTHESIS APPARATUS

(75) Inventor: Roger P. Jackson, Prairie Village, KS (US)

(73) Assignee: Medtronic Sofamor Danek, Incorporated, Memphis, TN (US)

(*) Notice: Under 35 U.S.C. 154(b), the term of this patent shall be extended for 0 days.

This patent is subject to a terminal disclaimer.

(21) Appl. No.: 09/123,052

(22) Filed: Jul. 27, 1998

(51) Int. Cl.⁷ ...................................... A61B 17/86
(52) U.S. Cl. .................. 606/73; 606/61; 411/3; 411/393
(58) Field of Search .................. 606/61, 65, 69, 606/72, 73; 411/3, 5, 393, 178, 407

(56) References Cited

U.S. PATENT DOCUMENTS

| D. 200,217 | 2/1965 | Curtiss . |
| 791,548 | 6/1905 | Fischer . |
| 2,201,087 | 5/1940 | Hallowell . |
| 2,239,352 | 4/1941 | Cherry . |
| 2,295,314 | 9/1942 | Whitney . |
| 2,532,815 | 12/1950 | Kindsvatter . |
| 2,553,337 | 5/1951 | Shafer . |
| 2,778,265 | 1/1957 | Brown . |
| 2,877,681 | 3/1959 | Brown . |

(List continued on next page.)

FOREIGN PATENT DOCUMENTS

| 3630863 | 3/1988 | (DE) . |
| 373809 | 5/1989 | (DE) . |
| 195455 | 9/1986 | (EP) . |
| 172130 | 2/1987 | (EP) . |
| 276153 | 7/1988 | (EP) . |
| 465158 | 1/1992 | (EP) . |
| 2467312 | 4/1981 | (FR) . |
| 203508 | 9/1923 | (GB) . |
| 834787 | 5/1960 | (GB) . |
| 92/03100 | 3/1992 | (WO) . |
| 94/10927 | 5/1994 | (WO) . |
| 94/10944 | 5/1994 | (WO) . |
| 96/06576 | 3/1996 | (WO) . |

OTHER PUBLICATIONS

Two Drawings of Sofamor dated Mar. 10, 1994 and Sep. 20, 1994.

Primary Examiner—Michael Buiz
Assistant Examiner—David O. Reip
(74) Attorney, Agent, or Firm—Woodard, Emhardt, Naughton, Moriarty & McNett

(57) ABSTRACT

An improved set screw with a break off head for use in an osteosynthesis apparatus. The set screw comprising a head or stem preferably having a hexagonal external cross-section, a lower portion having a thread extending around an outer surface thereof and a shank connecting the head to the threaded lower portion. An outer diameter of the shank is equal to a minor diameter of the threaded lower portion, i.e. the outer diameter of the threaded lower portion at the base of the thread. A bore extends into the set screw from an upper surface thereof. The bore has a first bore section and a second bore section wherein the second bore section has a reduced diameter relative to the first bore section and is separated from the first bore section by an internal shoulder. The internal shoulder extends into the bore below an upper end of the thread. The first bore section is sized relative to the shank to result in shearing of the head from the lower portion upon application of a pre-selected torque on the head relative to the lower portion. The stepped down bore configuration also facilitates use of an easy out tool for removing the threaded lower portion, if necessary, from an implant in which it has been secured. The bore may include a plurality of bore sections of increasingly smaller diameter to further facilitate use of an easy out tool.

14 Claims, 4 Drawing Sheets

U.S. PATENT DOCUMENTS

| | | |
|---|---|---|
| 2,927,332 | 3/1960 | Moore . |
| 3,143,029 | 8/1964 | Brown . |
| 3,370,341 | 2/1968 | Allsop . |
| 3,498,174 | 3/1970 | Schuster et al. . |
| 3,584,667 | 6/1971 | Reiland . |
| 3,812,757 | 5/1974 | Reiland . |
| 3,963,322 | 6/1976 | Cryctko . |
| 4,269,246 | 5/1981 | Larson et al. . |
| 4,492,500 | 1/1985 | Ewing . |
| 4,506,917 | 3/1985 | Hansen Arne . |
| 4,763,644 | 8/1988 | Webb . |
| 4,764,068 | 8/1988 | Crispell . |
| 4,790,297 | 12/1988 | Luque . |
| 4,838,264 | 6/1989 | Bremer et al. . |
| 5,073,074 | 12/1991 | Corrigan et al. . |
| 5,129,388 | 7/1992 | Vignaud et al. . |
| 5,147,360 | 9/1992 | Dobousset . |
| 5,261,912 | 11/1993 | Frigg . |
| 5,282,707 | 2/1994 | Palm . |
| 5,364,400 | 11/1994 | Rego, Jr. et al. . |
| 5,382,248 | 1/1995 | Jacobson et al. . |
| 5,496,321 | 3/1996 | Puno et al. . |
| 5,499,892 | 3/1996 | Reed . |
| 5,507,747 | 4/1996 | Yuan et al. . |
| 5,562,663 | 10/1996 | Wisnewski et al. . |
| 5,630,816 | 5/1997 | Rokegem et al. . |
| 5,643,260 | 7/1997 | Doherty . |
| 5,653,710 | 8/1997 | Harle . |
| 5,697,929 | 12/1997 | Mellinger . |

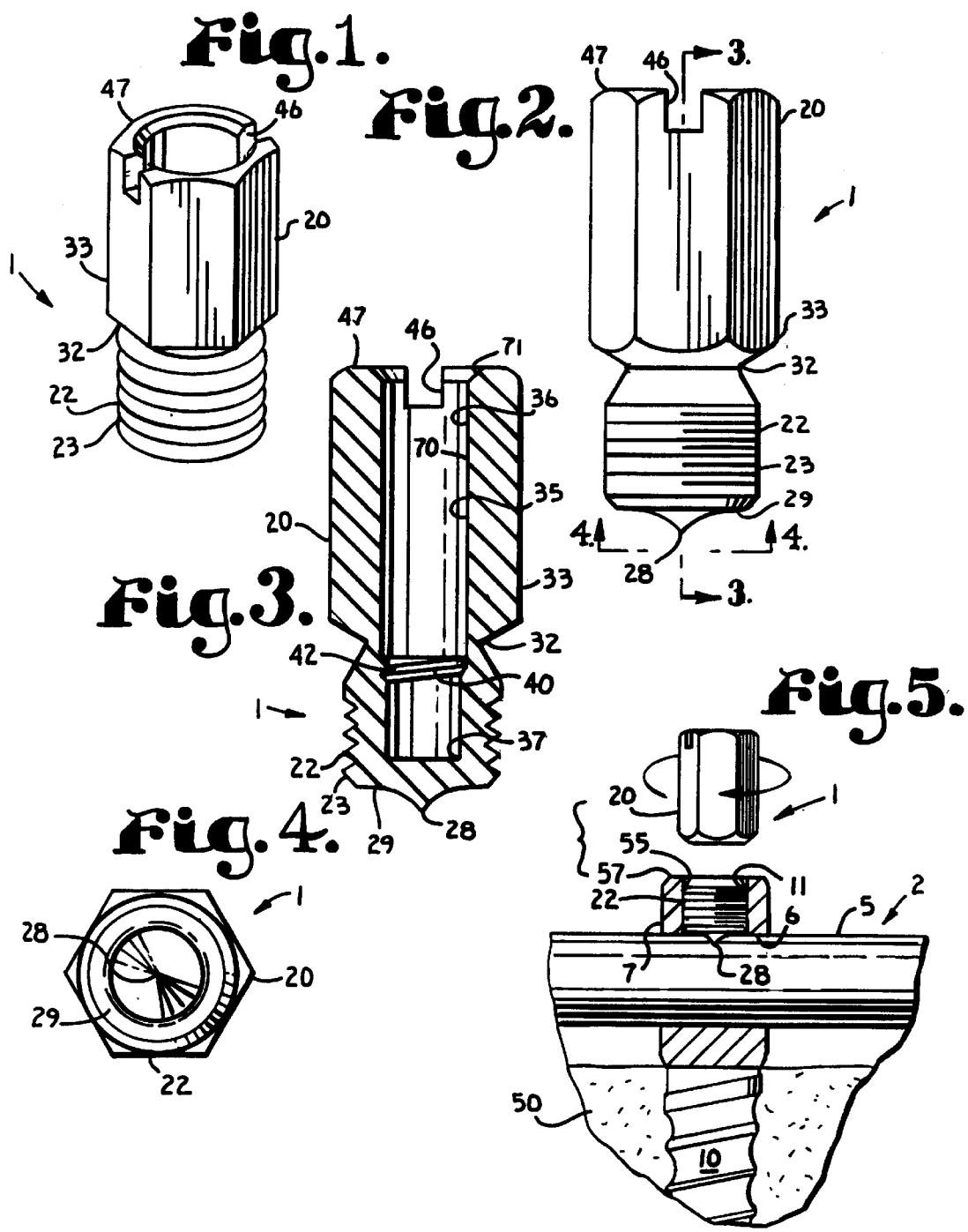

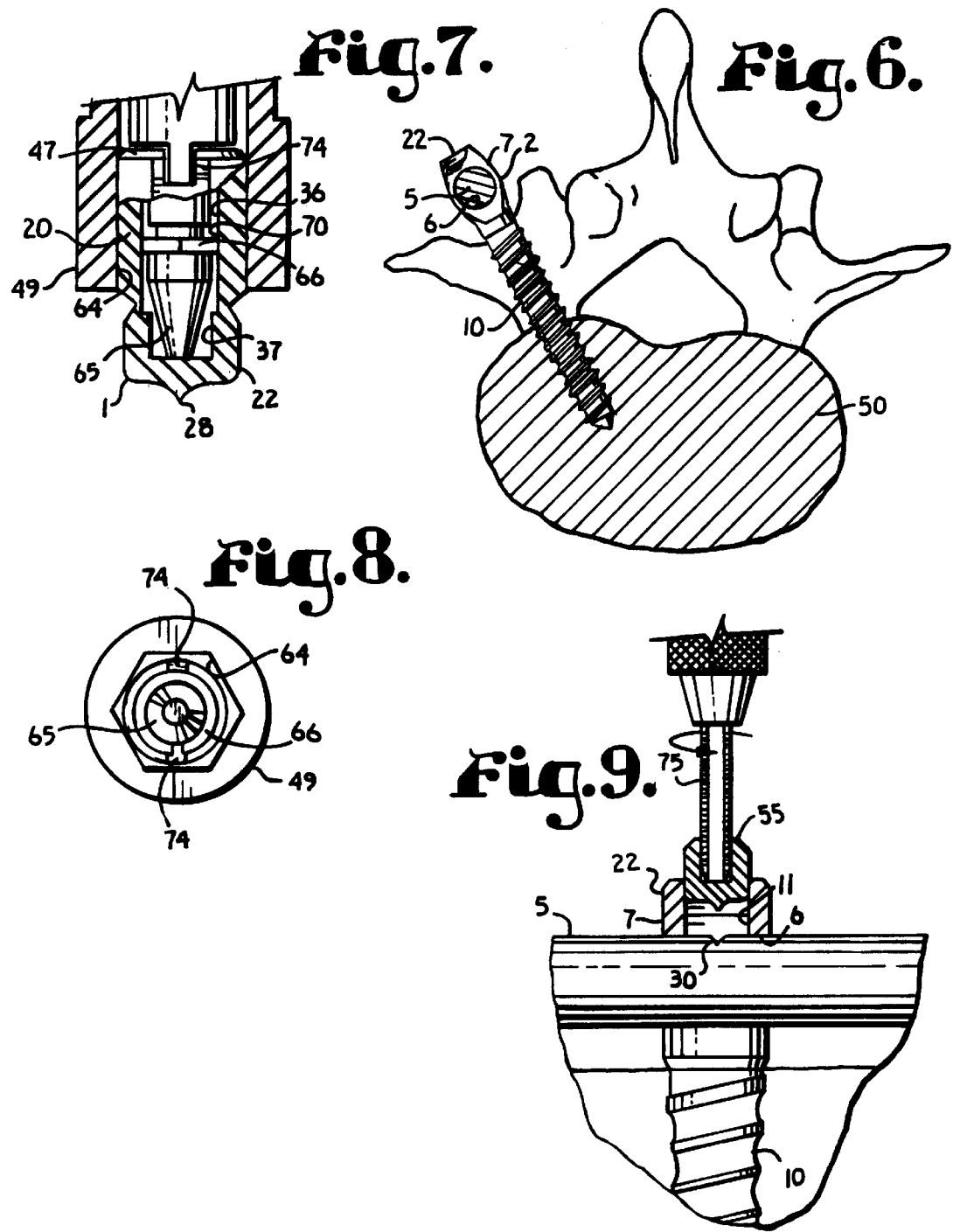

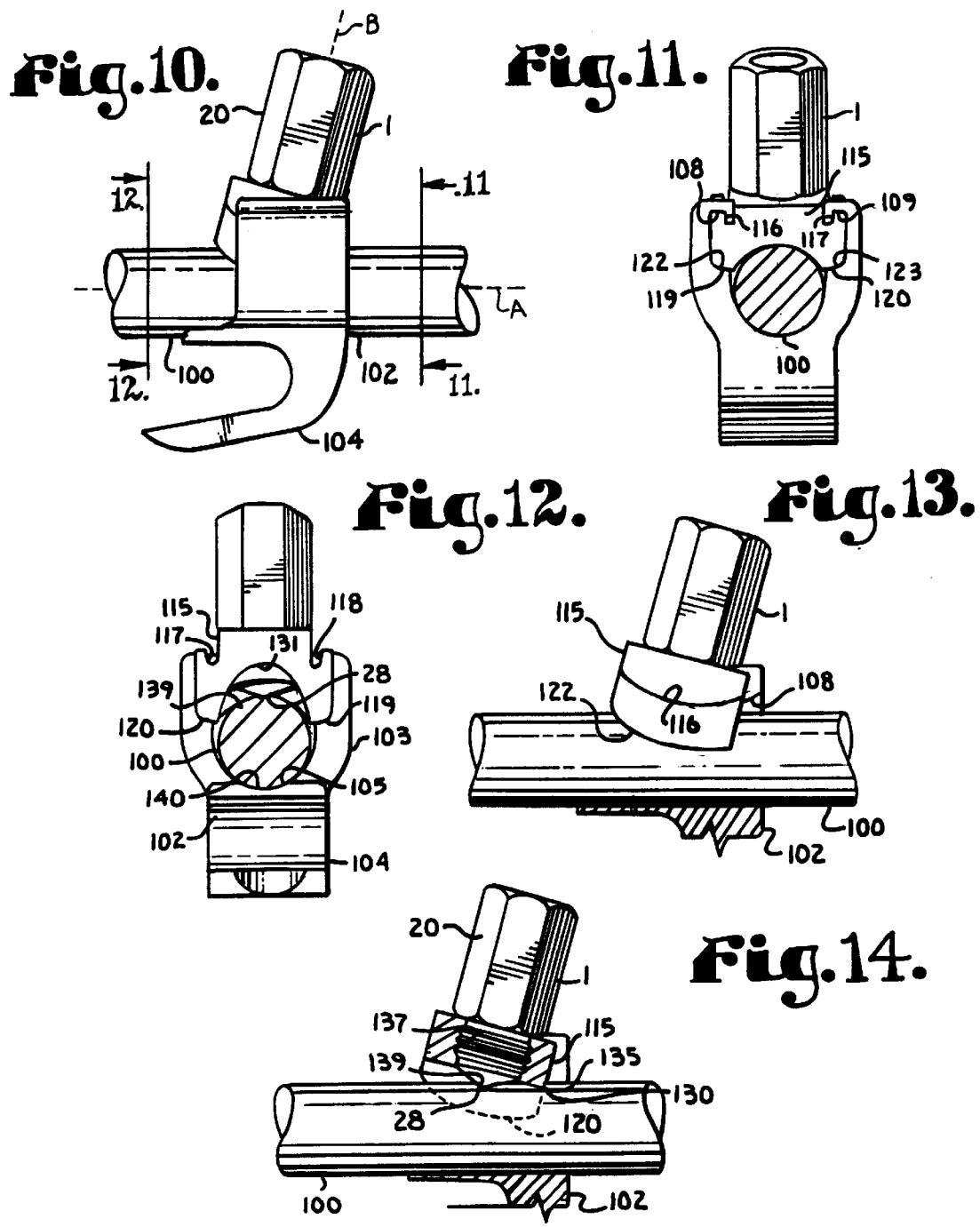

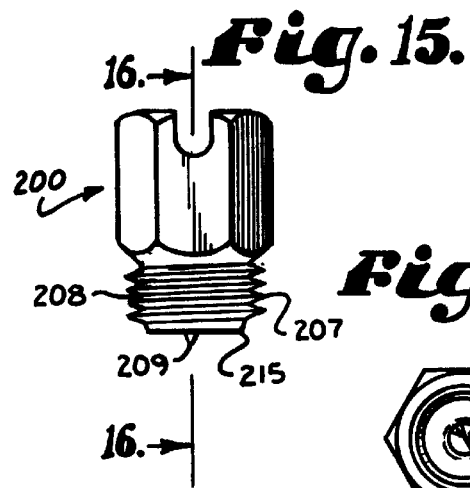
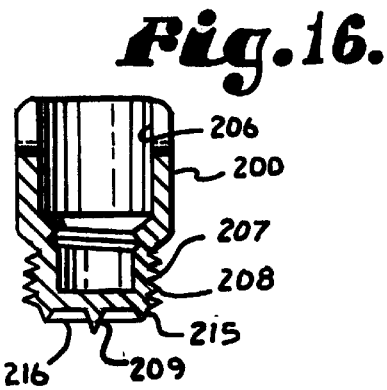
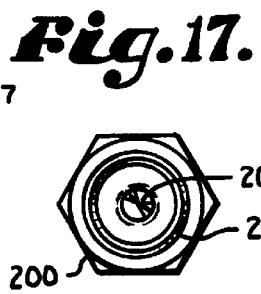
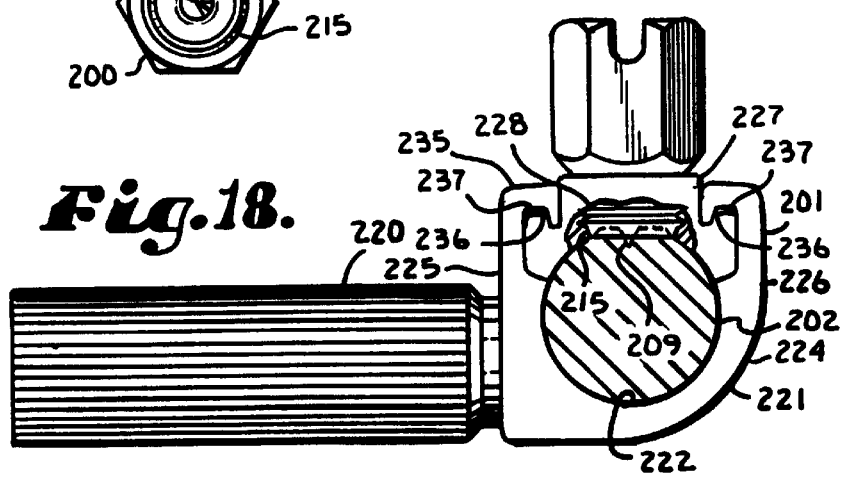
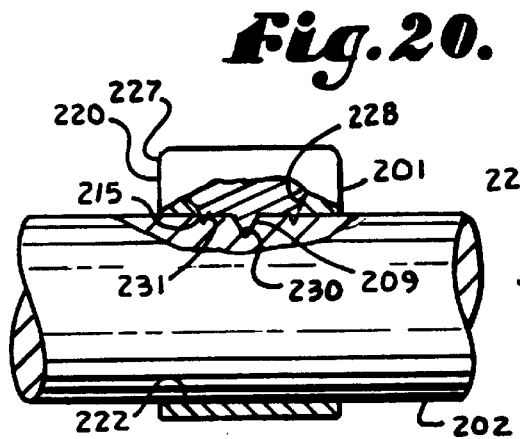
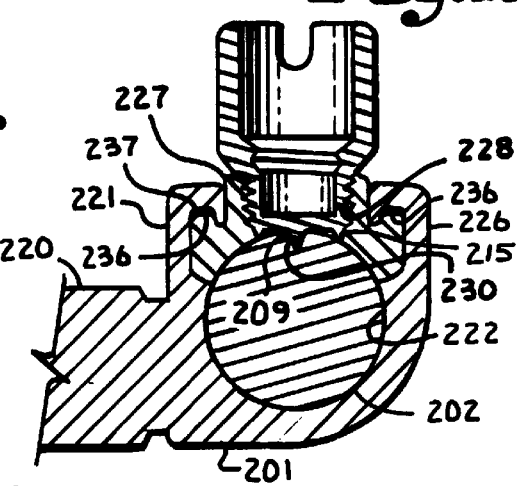

SET SCREW FOR USE WITH OSTEOSYNTHESIS APPARATUS

CROSS-REFERENCE TO RELATED APPLICATION

This application claims the benefit of U.S. patent application, Ser. No. 08/778,765, now U.S. Pat. No. 6,004, 349, filed Jan. 6, 1997 and entitled, "Set Screw for Use with Osteosynthesis Apparatus", which is hereby incorporated by reference in its entirety.

BACKGROUND OF THE INVENTION

The present invention relates to improvements in set screws for use with apparatus for correcting orthopedic deformities and, in particular, for use in spinal osteosynthesis.

Surgically implanted spinal osteosynthesis apparatus often includes rods which are secured along at least a portion of the spine by a system of hooks, bone screws including sacral screws and pedicle screws and transverse connectors for the purpose of stabilizing and adjusting spinal alignment. In a very basic apparatus of this type, the hooks and bone screws include a spinal rod bore extending through a ring or body or head of the hook or screw. The screws are screwed into the pedicle portion of the vertebra at desired locations and a spinal rod is then extended through the spinal rod bore in each bone screw.

Where the bone screw has a rod receiving ring and the rod is to be fixed in position in the ring, a set screw is inserted in a threaded bore extending through a wall of the ring, so as to engage the rod, and is then tightened to fix the translational and rotational relationship of the rod within the ring. The rods may then be bent or shaped to maintain an adjacent portion of the spine in a desired configuration, to provide support to the spine and to exert desired corrective or stabilizing forces on the spine.

A slightly more complicated system uses transverse connectors in association with the bone screws to secure the spinal rods. The transverse connectors include an arm and a head. The head has a spinal rod bore extending therethrough. The arm of the connector is inserted through the spinal rod bore in the pedicle screw then the spinal rod may be inserted through the spinal rod bore in the transverse connectors. A threaded bore extends through the head of the connector perpendicular to the axis of the spinal rod bore. Once the rod is inserted through the bore in the transverse connectors the set screws are inserted through the threaded bores and tightened to fix the relative position of the rod within the spinal rod bore and set screws are inserted in the threaded bores and tightened to fix the position of the transverse connector with respect to the pedicle screws.

The pedicle screws and transverse connectors may be of the closed type as discussed above or of an open end type wherein the head of the screw or connector generally incorporates a U-shaped groove. Several types of open end type bone screws have been previously used. One type of such screw is shown in the U.S. Pat. No. 5,005,562 of Cotrel. The device in the Cotrel patent has threaded interior surfaces on the two upright branches that form the rod receiving channel therebetween and which receive a threaded set screw having a rod engaging point and outer ring. The set screw in Cotrel is tightened against the rod by advancing the set screw along the threads. However, this system has limitations. In particular, the ability of the set screw of Cotrel to grip and hold the rod is heavily dependent on the torque applied to the set screw during installation. Unfortunately, the torque is limited because too much torque will cause the branches to spread, thereby allowing the set screw to loosen and the implant to fail. Such failure can also occur when forces are applied to the implant during use, such as at time of muscular stress or during accidents when the back is jolted. To try to overcome this problem associated with the Cotrel device, the implant branches and set screw are increased in size to add strength and/or a retention ring is placed around the outside of the branches to reduce the likelihood of expansion. However, the strengthening adds substantial bulk to an implant and a ring adds bulk and complexity to the implant. In implants it is important to try to reduce bulk rather than add to it, as it is desirable for the implants to be as low profile as possible.

Rather than have a pair of branches joined only by a set screw or by a set screw and an exterior ring, a cap has been proposed which mates with the branches on opposite sides of the cap to prevent the branches from expanding radially outward upon application of torque to the set screw. The cap also closes off the open end of the bone screw after the rod is placed in the groove in the bone screw. The set screw is then inserted in a threaded bore in the cap and tightened to fix the position of the transverse connector with respect to a respective bone screw. A substantial torque can then be applied to the set screw while held in the surrounding threads of the cap without expanding the bone screw branches.

Various implants such as hooks, pedicle screws and transverse connectors used in the present invention may be of the closed type, as discussed above, or of an open end type, such as described above, wherein the head of the hook screw or connector generally incorporates a U-shaped groove or slot, an upper end of which may be closed off by a cap after a rod is placed in the open end so as to complete the rod bore. A threaded screw bore for the set screw typically extends through the cap.

The efficacy of the set screw is critical to the overall performance and efficiency of the osteosynthesis apparatus. The set screw must firmly secure the spinal rod or the arm of transverse connectors to prevent rotational or translational movement of the rod or arm after installation. Due to the nature of use of the set screw, it is important that the set screw be relatively small yet constructed to receive sufficiently high torque to firmly set the set screw and hold the rod. The set screw must also be easily manipulated to permit relatively rapid insertion and tightening during surgical procedures. It is also preferable that after insertion, no portion of the set screw extends beyond the threaded bore into which the set screw is inserted. The remaining portion of the set screw should be removable to facilitate disassembling of the osteosynthesis apparatus at any time. It is desirable that the set screw take advantage of physical penetration into the rod so as to improve the strength of the connection to resist axial movement of the rod relative to the set screw over that provided only by abutting friction.

Set screws have been previously developed with break-off heads or stems which break off after the set screw is inserted through a threaded bore and tightened to a preselected torque. Preferably, no portion of the set screw that remains after the head or stem breaks off extends above or beyond an outer edge of the threaded bore. However, prior art set screws normally have undesirable burrs that are left after the head breaks off that must be removed, thereby making the procedure more difficult or alternatively such burrs may lead to irritation of the patient, if not removed. Often, after installation, a set screw must be removed to reposition a rod or fix a broken apparatus. Prior art set screws have been difficult to remove after the head or stem is broken off. Consequently, it is desirable to have a set screw that can be comparatively easily removed even without a head.

It is also desirable to have a set screw that has an axially aligned tip that penetrates relatively deeply into a rod for preventing movement along or around the rod of an associated implant once tightened, but also includes structure that helps prevent rocking or translational movement of the set screw relative to the point of penetration. Rocking or movement of the screw relative to the location of penetration weakens the grip provided by the tip in the rod and the prevention of such movement substantially strengthens the juncture of the screw and the rod. The set screw tip, such as a point can only penetrate deeply into the rod if sufficient torque can be applied to the set screw to do so. In general greater torque is available due to greater bulk or due to special construction that allows greater strength without adding bulk. The latter is preferred in implants.

In general, there is still a need for an improved set screw which is quite strong in size, reliable in securing an osteosynthesis apparatus in place without burrs or high profile, is easily removable and is relatively small yet easily manipulable to facilitate its insertion and removal.

SUMMARY OF THE INVENTION

The present invention comprises an improved set screw for use in an osteosynthesis apparatus. The set screw is adapted for use in securing a rod or elongate member in a bore of a ring or head of an implant or within a channel in an open headed implant from translational or rotational motion. The ring or ringlike structure formed by an open head with a closure cap is of the type formed in the head of a hook, the head of a bone screw, the head of a connector secured to the bone screw or other type of implant to which a rod is secured. The rod is of the type including spinal rods or the rod portion of a connector which may be round, square or otherwise shaped in cross-section and which has an elongate axis.

A threaded set screw bore extends generally radially through a wall of the ring or head where the implant has a closed head or through a threaded bore in a cap used in conjunction with an "open" head, so as to normally be aligned such that a central axis of the set screw intersects with the elongate axis of the rod or member receiving bore associated with the ring or head of the closed hook, screw or connector. In some instances the axis of the set screw will be perpendicular to an axis of the rod; but in some use the axis of the set screw, while intersecting with the axis of the rod will be non-perpendicular thereto.

The set screw has a head or stem preferably having a hexagonal external cross-section, and a lower portion having a threaded outer surface. A tip is centrally formed on a lower surface of the set screw so as to be coaxially aligned with the axis of the set screw. A peripheral break notch preferably is formed between the head and the lower threaded portion of the set screw to facilitate breaking and separation of the two portions. A cylindrical bore preferably is formed in the set screw and extends through the head or stem and partially, but not completely, through the lower threaded portion.

The set screw is especially effective in conjunction with open headed implants such as bone screws. The set screw is utilized in conjunction with a cap having opposed slots which mate and lock with opposed slots on respective branches of the implant to prevent spreading or separation of the branches once the cap is in position on the head. The set screw is threadably received in an entirely surrounding bore in the cap so as to stabilize the threaded portion of the set screw while torque is applied to the set screw and as the set screw tip or point drives or penetrates into the rod. In a preferred embodiment the set screw includes a tip and a ring having a sharp lower edge that encircles the point and penetrates into the rod to further stabilize the resulting structure.

In use, after the rod is positioned in the ring or ringlike structure, the set screw is tightened or advanced in the set screw bore by a socket type wrench or other suitable driver such that the tip or point engages and bites or penetrates into the outer surface of the rod, while biasing an opposite side of the rod against a side wall of the ring so as to fix the position of the rod relative to the ring, that is, to prevent translational or rotational movement of the rod relative to the ring. Preferably, further tightening of the set screw causes the head or stem to shear off along the peripheral notch preferably without burrs and at a preselected and desired consistent torque that is sufficiently high to allow for considerable penetration of the tip or point into the rod and such that the axis of the set screw generally intersects the elongate axis of the rod or member.

In the break off head set screw, the cylindrical internal bore in the set screw includes an upper bore section and a lower bore section. The upper bore section generally extends coaxial with the head or stem of the set screw and the lower bore section extends partially through the lower threaded portion of the set screw. The upper bore section is adapted to facilitate removal of the set screw head or stem once it is sheared off.

In the break off head set screw, the set screw is adapted for use with a socket type wrench having a male member or projection extending centrally in the wrench socket that mates with the set screw internal bore. The projection has an outwardly extending biasing element thereon. The projection is sized for insertion into at least the upper bore section when the head or stem of the set screw is positioned in the socket. The biasing element biases against the internal wall of the head defining the upper section of the cylindrical bore to help grip the head. The socket type wrench applies torque to the head until a preselected torque is achieved at which time the notch directs the location or point of breakage and the head breaks from the remainder of the screw without leaving substantial burrs or the like extending above the surface of the ring.

In the break off head set screw, after sufficient torque is applied and the head or stem of the set screw is sheared off, the lower bore section is adapted to receive an easy out type tool to permit removal of the set screw lower threaded portion, if necessary. The lower bore section in some embodiments is of a smaller diameter than the upper bore section. A partial reverse starter thread, of at least one half turn, is in some instances formed inside a section of the internal wall of the bore of the set screw defining the lower bore section near an upper end thereof. The reverse thread facilitates gripping and thus starting the easy out type tool to allow the easy out type tool to be used to remove the lower portion of the screw after the head or stem has been broken off. In certain embodiments the side wall of the set screw is threaded which increases breakoff torque and which in some instances provides sufficient wall thickness for an easyout to obtain purchase in the remaining wall without the starter thread.

As noted above in a particular embodiment of the invention, the set screw is used in conjunction with a cap utilized to close an open ring or body surrounding a rod or other elongate member. Caps of this type have a pair of curved ears or slot followers that slideably are received in slots in opposite sides of branches forming the remainder of the ring at an opening to be filled by the cap. The ears slideably lock with the slots so as to prevent radially outward separation of the branches when torque is applied to the set screw or other forces are applied to the implant.

The cap has a central threaded bore to receive a set screw such that the axis of the set screw is positioned to intersect the longitudinal axis of a rod or other member surrounded by the ring. Normally, the slots and ears are aligned such that the ears of the cap can easily slide into the slots from one side, but are tapered so that the ears are trapped by the slots on the opposite side and effectively form a stop to limit movement or prevent removal of the cap from the remainder of the ring from the opposite side. The cap also has a front edge that may be rotated relatively toward the rod when the cap is pushed such that the ears thereof are as deep as possible into the slots of the remainder of the ring.

When the ears are positioned as deeply as possible in the slots and the set screw is tightened against the rod or member, the set screw tip or point penetrates into the rod and the front edge of the cap also engages and wedges against the surface of the rod. The penetration of the tip and wedging of the edge are partially opposed such that, if forces try to move the rod along the axis thereof relative to the ring after the set screw is tightened in a first direction, then such movement is opposed especially by the tip of the set screw, and if forces try to move the rod in the opposite direction such movement is opposed especially by the edge of the cap wedging more tightly and then biting into the surface of the rod.

In a second embodiment a ring having a lower sharp edge encircles the axial point of the screw and penetrates into the rod during use to help prevent movement of the set screw relative to the rod and to thereby help stabilize a set screw that is aligned perpendicularly relative to the major axis of the rod.

OBJECTS AND ADVANTAGES OF THE INVENTION

The objects and advantages of the invention include: providing a locking mechanism with set screw for use in an osteosynthesis apparatus for securing a rod or elongate member from rotational and translational movement within a bore of a securement ring or body; providing such a set screw which is relatively small, yet which can be readily manipulated; providing such a set screw which includes a head or stem which breaks off during tightening at a preselected torque after the set screw has been tightened down; to provide such a set screw which includes a peripheral break inducing and directing notch on an outer surface of the screw between the head or stem of the screw and a lower threaded portion thereof; to provide such a set screw which includes a tip or point for biting or penetrating into the rod to be secured by the set screw; to provide such a set screw incorporating means for facilitating removal of the head of the set screw after it has been broken off; to provide such a set screw which incorporates means for facilitating removal of the lower threaded portion of the set screw when desired; to provide such a set screw having a cylindrical bore extending partially therethrough; to provide such a set screw having an upper bore section extending through the head or stem of the set screw and a lower bore section extending partially through the lower threaded portion of the set screw; to provide such a set screw to be used in cooperation with a cap for completing a ring such that the cap prevents separation of opposite branches of an implant forming a portion of the ring; to provide such a set screw and cap combination wherein the point of the set screw penetrates into the rod and especially resists movement of the rod relative to the ring in a first direction and wherein the cap is rotated to have an edge that is urged to wedge and in some instances to bite into the rod under load by tightening the set screw such that the edge resists movement of the rod relative to the ring in a second direction; to provide such a set screw having a ring with a lower sharpened edge encircling an axially aligned point of the set screw and which during usage penetrates the surface of the rod that is also penetrated by the point so as to stabilize and help prevent movement of the screw relative to the rod once the screw is tightened; and to provide such a set screw which is relatively simple to manufacture and particularly well suited for its intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a set screw in accordance with the present invention.

FIG. 2 is a front elevational view of the set screw of the present invention;

FIG. 3 is a cross-sectional view, of the set screw, taken along line 3—3 of FIG. 2.

FIG. 4 is a cross sectional view of the set screw, taken generally along line 4—4 of FIG. 3.

FIG. 5 is a front elevational view on a reduced scale of the set screw showing a lower threaded portion of the set screw engaging a spinal rod secured within a spinal rod bore in a bone screw and showing a head or stem of the set screw after being broken off.

FIG. 6 is a side elevational view on a reduced scale of a bone screw secured within a vertebra and with portions broken away to show a lower threaded portion of the set screw of the present invention secured within the bone screw.

FIG. 7 is a fragmentary front elevational view of the set screw shown secured within a socket wrench with portions broken away to show detail.

FIG. 8 is a bottom plan view of the socket wrench, as shown in FIG. 7, without a set screw secured therein.

FIG. 9 is a front elevational view similar to FIG. 5 showing use of an easy out type tool to remove a lower threaded portion of the set screw of the present invention from a bone screw.

FIG. 10 is a fragmentary side elevational view of the set screw utilized in conjunction with an open ring hook and a cap for the hook showing a ring of the hook completed by the cap and the hook secured to a rod.

FIG. 11 is a fragmentary cross-sectional view of the set screw, hook and cap, taken along line 11—11 of FIG. 10.

FIG. 12 is a fragmentary cross-sectional view of the screw, hook and cap, taken along line 12—12 of FIG. 10.

FIG. 13 is a fragmentary side elevational view of the set screw, hook and cap, showing the cap complete but with a portion of the ring broken away to illustrate details.

FIG. 14 is a fragmentary side elevational view of the set screw, hook and cap, showing portions of the ring and cap broken away to illustrate position of the set screw and cap engaging the rod after the set screw is tightened to a torque just prior to a head of the set screw breaking therefrom.

FIG. 15 is a side elevational view of a modified set screw in accordance with the present invention.

FIG. 16 is a cross-sectional view of the modified set screw, taken along line 16—16 of FIG. 15.

FIG. 17 is a bottom plan view of the modified set screw.

FIG. 18 is a side elevational view of the modified set screw partially securing a rod in an implant extension with portions broken away to show detail thereof.

FIG. 19 is a cross-sectional view of the modified set screw and extension, showing internal detail of the set screw prior to removal of a head thereof.

FIG. 20 is a front elevational view of the modified set screw and extension after removal of the head of the set screw with portions broken away to show detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally refers to a set screw for use in osteosynthesis apparatus and in particular for use in spinal osteosynthesis apparatus 2. As shown in FIGS. 5 and 6, the set screw 1 is adapted for use in securing a rod 5 of the apparatus 2 relative to a rod receiving bore 6 of a head or ring 7, from translational or rotational motion. The ring 7 is of the type formed in the head of a bone screw 10 or the head of a connector or bone hook (not shown) secured to the bone screw 10. In the field of spinal osteosynthesis, the bone screws 10 are often referred to as sacral screws or pedicle screws. The rod 5 may be of the type including spinal rods or the arm or rod portion of a connector. The illustrated rod 5 is round; however, it is foreseen that the rod could be square to help prevent rotation in a similarly shaped bore in the bone screw 10, or have a cross section of almost any shape. A threaded set screw receiving bore 11 extends through the ring 7 perpendicular to the axis of the rod receiving bore 6 and extends radially relative to the ring 7 for the closed hooks, screws and connectors. For open hooks, screws and connectors the angle of point of penetration on the rod may vary with respect to the axis of the rod and to the design for a closing cap thereof.

The set screw 1, as is shown in FIGS. 1 through 4, comprises a head or stem 20, of hexagonal external cross-section and round internal cross section, and a lower portion 22, having a threaded outer circumferential surface 23. The head 20 is relatively elongated to facilitate manipulation of the set screw 1. A tip, illustrated as a point 28, is formed on a lower surface 29 of the set screw 1 centrally thereof so as to extend outward along a central axis of rotation of the set screw 1. The point 28 forms a point receiving notch, depression, or indentation 30 in the rod 5. A peripheral break inducing notch 32 is formed between the head 20 and the lower threaded portion 22 of the set screw 1 on an outer surface 33 of the set screw 1. The notch is positioned and sized to initiate breakage along the radially innermost portion thereof at this level and at a preselected torque without forming substantial burrs on the resulting upper surface of the set screw lower portion 22.

As best seen in FIG. 3, a cylindrical bore or projection receiving bore 35, comprising an upper bore section 36 and a lower bore section 37 is formed in the set screw 1 and extends through the head 20 and partially through the set screw lower threaded portion 22. The upper bore section 36 generally extends coaxial with the head 20 of the screw 1 and the lower bore section 37 extends partially through the lower threaded portion 22 of the screw 1. The lower bore section 37 is of slightly smaller diameter than the upper bore section 36. A reverse thread 40, of preferably at least one half turn, is formed along an internal wall 41 of the set screw 1 defining the lower bore section 37 near an upper end 42 thereof, see FIG. 3.

A drive slot 46 is located at a top end 47 of the set screw head 20. The slot 46 is a rectangular notch extending downward in FIG. 3 from the top end 47 with portions on diagonally opposite sides of the screw 1. The set screw 1 is preferably driven by a hexagonal socket type wrench 49, partially shown in FIG. 7. The slot 46 can receive mating parts of the wrench 49; however, the drive slot 46 is adapted to also receive a set screw holder type tool for starting the set screw 1 into the threaded set screw bore 11 in some applications.

In use, the set screw 1 may be inserted in the set screw receiving bore 11 in the ring 7 after the bone screw 10 is inserted into a bone 50 of a patient and after a rod 5 is inserted through the rod receiving bore 6. To secure the rod 5 in position, thereby preventing further rotational or translational movement of the rod 5 with respect to the rod receiving bore 6, the set screw 1 is further driven through the set screw receiving bore 11 until the point 28 engages and bites into the rod 5 at depression 30. Further driving or tightening of the set screw 1 produces a preselected torque on the head 20 and causes the head 20 of the set screw 1 to shear off along the radially innermost portion of the peripheral notch 32, as shown in FIG. 5. The bore 11 and the penetration of the point 28 into the depression 30 stabilizes the set screw 1 relative to the rod 5, so that the set screw 1 is able to secure the rod 5 and prevent relative movement of the rod 5 with respect to the bone screw 10 even under substantial load.

The lower threaded portion 22 of the set screw 1 is preferably sized such that after the head 20 is sheared off, an upper surface 55 of the set screw lower portion 22 is generally flush with an upper edge or upper surface 57 of the ring 7 such that no portion of the set screw lower portion 22 extends beyond the upper surface 57 of the ring 7. Further, after the head 20 is sheared off, the upper surface 55 of the set screw lower portion 22 is generally free from burrs or jagged edges.

The set screw 1 may also be pre-loaded into the bone screw 10, or related structure, prior to insertion into the patient. In particular, the set screw 1 may be manually inserted in the threaded set screw receiving bore 11 of a bone screw 20 or a connector before insertion in a patient and rotated a sufficient number of turns such that the set screw 1 is secured in the set screw receiving bore 11, but such that the point 28 does not extend substantially into the rod receiving bore 6. The bone screw 10, with the set screw 1 secured thereto, may then be secured into the appropriate bone 50 of a patient. After a rod 5 is inserted through the rod receiving bore 6 of the bone screw 10. Thereafter, the set screw 1 is tightened, as discussed above.

The upper bore section 36 of the set screw 1 is adapted to facilitate removal of the set screw head 20 once it is sheared off from the lower threaded portion 22. The set screw is adapted for use with the socket type torque wrench 49, as shown in FIGS. 7 and 8, having a hexagonal socket 64 and a male member or projection 65 extending centrally in the socket. The projection 65 includes a resilient biasing member 66 circumferentially secured thereon. The projection 65 is sized for insertion into at least the upper bore section 36 when the set screw head 20 is positioned in the socket 64. The resilient biasing member 66 biases against an internal wall 70 of the head 20 defining the upper bore section 36 to grip the head 20.

The internal wall 70 has a chamfer 71 at the top end 47 of the set screw head 20 to facilitate insertion of the projection 65 into the projection receiving bore 35 in part by facilitating compression of the resilient biasing member 66. The resilient biasing member 66, as shown in FIGS. 7 and 8, generally comprises a split washer type spring, however it is foreseen that the biasing element 66 may be of a wide range of configurations and structures. Further other retention means for releasably securing the set screw 1 to the projection 65 may be utilized including a rubber washer, magnetic coupling means, and various structure producing an interference fit between the projection 65 and the projection receiving bore 35.

The projection 65 may include a pair of drive projections or tabs 74 extending laterally from opposite sides of the projection 65 and adapted to mate with the drive slot 46 extending across the top end 47 of the set screw head 20 to permit an installing surgeon to drive or rotate the set screw 1 by the projection 65.

After the head 20 has been sheared off from the set screw lower threaded portion 22, the lower bore section 37 is adapted to receive an easy out type tool 75 to permit removal of the set screw lower portion 22 when necessary and as is shown in FIG. 9. The reverse thread 40 facilitates starting the easy out type tool 75 by allowing the tool 75 to get an initial grasp after which it would be expected to cut further into the lower bore 37.

The bone screws 10 and related connectors (not shown) discussed above are of a closed end variety in that the ring 7 is of one piece construction. The set screws 1 of the present invention are also adapted for use with bone screws and connectors of the open end variety (not shown). In the open end variety, the ring 7 includes a generally U-shaped groove opening along an upper end of the head or ring 7. A saddle or cap is securable to the head 7 to close off the groove and form the rod receiving bore 6. The set screw receiving bore 11 may be formed in the cap or another part of the head 7.

Shown in FIGS. 10 through 14 is a modified embodiment of apparatus of the invention utilizing the set screw 1 described above.

In particular, FIGS. 10 through 14 show an elongate implant first member, here a rod 100 having a central elongate axis designated by the reference numeral A. The screw 1 is as described above and has a central axis B. The axes A and B intersect subsequent to assembly, as is shown in FIGS. 10 through 14, although at an angle that is not a right angle.

The set screw 1 is utilized in conjunction with a second member, here an implant hook 102, having a hook body or head 103 and a hook finger portion 104. The head 103 is somewhat U-shaped forming a central partial bore 105 surrounded by a partial ring 106. When the apparatus is assembled, the rod 100 is cradled by the bore 105 and the partial ring 106.

On opposite sides of the facing ends of the partial ring are curved or U-shaped slots 108 and 109. The slots 108 and 109 are not parallel but slightly converge to the left in the view seen in FIG. 10.

A cap 115 is located so as to complete the ring initiated by the partial ring 106. The cap 115 has a pair of slot followers or ears 116 and 117 that are sized and shaped to be received in the slots 108 and 109 respectively. The ears 116 and 117 are parallel and do not converge and are curved to conform to the curve of the slots 108 and 109. The lower ends 119 and 120 of each side of the cap 115 are curved and are received by simultaneously curved shoulders 122 and 123 on opposite sides with the partial ring 106. The cap 115 is united with the partial ring 106 by inserting the ears 116 and 117 of the cap 115 into the slots 108 and 109 of the partial ring 106 from the right side as seen in FIG. 10. The cap 115 is then partially rotated to the left (again as viewed in FIG. 10) by allowing the cap lower ends 119 and 120 to slide on the shoulders 122 and 123 respectively until the convergence of the slots 116 and 117 binds with the ears 108 and 109 so as to limit further relative movement of the cap to the left in FIG. 10 and operably function as a stop. This bound position is seen in FIGS. 10 through 14. It is foreseen that a stop can be provided by other structure and function within the concept of the invention. When the cap 115 is located so as to complete the partial ring 106, the cap 115 prevents lateral separation of opposite branches forming the partial ring 106 when torque or lateral forces are applied thereto.

The cap 115 has a rear edge 130 and a front edge 131. When the cap 115 is in or near the bound position, the front edge 131 engages and partially penetrates into the rod 100, as is seen in FIG. 14, as the set screw 1 is tightened. This penetration forms a notch 135 into the rod 100.

The cap 115 has a centrally located threaded bore 137 that receives the threaded lower portion 22 of the set screw 1, as is seen in FIGS. 10 through 14.

As the set screw 1 is advanced in the cap bore 132 the set screw tip or point 28 advances toward and eventually engages the rod 100. The set screw 1 is torqued until the point 28 penetrates the rod 100 so as to produce a point receiving depression or notch 139 in the rod 100. In this manner both the point 28 and the cap front edge 130 penetrate the rod 100. The set screw 1 also biases the rod 100 against a side wall 140 of the partial ring 106. The surrounding nature of the cap bore 132 relative to the set screw 1, as seen in FIG. 14, in conjunction with the penetration of the point 28 into the rod 100 and the engagement of the cap edge 131 with the rod 100 forms a very stable configuration that substantially resists movement of the rod 100 relative to the implant hook 102 even when substantial forces are applied through use or accident to cause relative movement.

As seen in FIG. 14, if forces urge the rod 100 to the left relative to the partial ring 106, then the cap front edge 130 especially resists relative movement, and if forces urge the rod 100 to the right relative to the partial ring 106, then the set screw point 28 especially resists relative movement. As has been discussed before the upper portion 20 of the set screw is subsequently removed by application of additional rotational force thereto until a preselected torque is achieved. In this manner the hook 102 is securely held to the rod 100 with relative good stability.

Shown in FIGS. 15 through 20 is a modified embodiment of a set screw in accordance with the present invention and generally represented by the reference numeral 200. The set screw 200 is shown in use with an implant extension 201 to secure a rod 202 in the extension 201.

The parts of the set screw 200 are in many ways quite similar to the parts of the set screw 1 except for size of parts relative to each other and except as noted below. Consequently, the set screw 200 will not be described in detail, but rather reference is made to the description of set screw 1 for detail not described here. The set screw 200 includes a head 205 with a central and axial bore 206, a lower portion 207 with an exterior thread 208 and a lower axially aligned point 209.

The main difference between the screw 1 and the screw 200 is the inclusion of a ring 215 positioned to encircle the point 209. The ring 215 extends 360 degrees around and is radially spaced from the point 209. A lower edge 216 of the ring 215 is sharpened and adapted to cut into the rod 202 when urged thereagainst. The point 209 preferably extends axially outward and downward further than the ring 215 so as to penetrate deeper into the rod 202 during use.

The illustrated extension 201 is a conventional extension having an elongate rod shaped member 220 fixedly attached to a ring member 221 having a central bore 222. The bore 222 is aligned perpendicularly with respect to a major axis of the rod shaped member 220.

The ring member 220 is two piece and includes a V-shaped portion 224 with a pair of arms or branches 225 and 226 aligned on opposite sides of the bore 222 and a closure cap 227. The cap 227 has a threaded bore 228 adapted to threadably receive the set screw 200, as seen in FIGS. 18 to 20.

The branches 225 and 226 each include facing and inwardly directed flange like structures 235 which form slots 236. Opposite sides of the cap 227 include slot followers 237 which are slideably received in respective slots 236 when the set screw 200 is in a non tightened state. The slot followers 237 are shown in the slots 236 in FIGS. 18, 19 and 20.

In use the set screw 200 is threaded into the receiving bore 223, such that the point 209 engages a rod 202 received in a bore 222 of the ring member 221. As the set screw 200 is tightened the point 209 penetrates the rod 202 and forms an indentation 230 in the rod 202, see FIG. 19. Preferably, the point 209 penetrates substantially into the rod 206. As the point 209 continues to penetrate the rod 206, the edge 216 of the ring 215 engages and then also penetrates the rod 202 so as to form a groove 231, although preferably not as deeply as the point 209. Torque is then further applied to the set screw 200 until a desired predetermined torque is applied to the set screw 200 at which time the head 205 breaks from the remainder of the screw 200 leaving the lower body 207 in the bore 228 and the point 209 penetrated into the rod 202. The ring 215 also partially penetrates into the rod 202.

When the set screw 200 is fully tightened, the cap 227 is biased away from the rod 202. This causes the slot followers 237 to snugly and tightly fit against the respective slots 236 into which they are received. This in turn secures and locks the cap 227 in position to complete a ring with the V-shaped portion 224. This also secures the branches 225 and 226 so as to prevent the branches from separating radially outward from each other so as to loosen the set screw 200 or the connection of the rod 202 to the connector 201 when stress is placed upon the implant due to strain or accident as well as when torque is applied to the set screw 200 during installation. The combination of the cap bore 228 holding the set screw acting in conjunction with the point penetration into the rod 202 by the point 209 and the penetration of the ring 215 into the rod 202 at least at two axially spaced locations on the rod 202 on opposite sides of the point 209, substantially stabilizes the set screw 200 relative to the rod 202 and greatly resist axial or rotational movement of rod 202 relative to the connector 201 once the set screw 200 has been fully torqued, as in FIG. 20.

The set screw body 207 can be removed from the bore 223 in the manner described for removing the set screw lower portion 22 from the position shown in FIG. 5.

It is foreseen that while a hook and connector have been described and illustrated in certain embodiments of the invention in conjunction with a cap, that the apparatus and method of joining an open ring that is completed with a cap with an elongate member such as a round rod, can be utilized with other devices using similar structure such as bone screws or connectors and that a first member having a non-round cross-section, such as a square cross-section, could be used.

It is noted that while the set screws of the present invention may be used in conjunction with knurled rod, knurlling causes the rod to be weakened and fail more easily. Therefore, it is normally preferable to use the set screws of the invention with smooth surface rod. The set screws of the present invention are especially effective in penetrating into and preventing relative motion between the set screw and smooth rod. In addition the set screws of the present invention can be applied with a relatively high torque because the bore in which the set screw is received is closed and completely surrounds the set screw so that it does not spread during torquing and such that the set screws of the present invention can relatively deeply penetrate into rod, especially smooth rod, and hold securely against relative movement while stabilizing the screw with respect to the rod, even when the screw is positioned in the closure cap of an open ended implant. The set screws of the present invention may also be relatively small, for example 5.5 mm. in diameter, and still provide a strong and stable positional stabilization of an associated implant relative to a rod received in the implant.

It is further noted that the stabilization system of the present invention may in some instances utilize a ring with a lower cutting edge to penetrate into a rod on diagonally opposed locations relative to the ring without including a point. Consequently, the set screw may have a tip that has a point and/or has a ring that in each case penetrates into the rod and that functions with the bore that surrounds the set screw to stabilize the structure.

It is also foreseen that in some specialized uses of the set screw that the set screw will be configured to incorporate a stabilizing structure, but that the head will not be removable, that is, broken from the remainder of the set screw upon application of torque. In such instances the head will normally be solid without an interior bore, but such a head could also include an interior bore for receiving a tool for guidance or control during installation.

It is to be understood that while certain forms of the present invention have been illustrated and described herein, it is not to be limited to the specific forms or arrangement of parts described and shown.

What is claimed and desired to be secured by Letters Patent is as follows:

1. A spinal implant set screw comprising:

a grippable upper portion;

a lower portion having an external thread;

a torque-limiting portion connecting said upper portion and said lower portion; and a cylindrical bore formed in said set screw and extending through at least a portion of said lower portion internal of said external thread and said torque-limiting portion, said cylindrical bore facilitating removal of said lower portion after said upper portion has been sheared off from said lower portion.

2. A spinal implant set screw as set forth in claim 1, wherein said torque-limiting area comprises a necked portion.

3. A spinal implant set screw as set forth in claim 1, wherein said torque-limiting area further includes an internal opening.

4. A spinal implant set screw as set forth in claim 1, wherein said torque-limiting area has a reduced cross-sectional area.

5. The set screw of claim 1 having at least one planar surface for external application of torque to said set screw.

6. The set of claim 1 wherein said cylindrical bore extends through said upper portion.

7. The set screw of claim 6 wherein said cylindrical bore comprises a first bore section and a second bore section; said first bore section being generally coextensive with said upper portion and said second bore section extending into said lower portion; said second bore section having a diameter comparatively smaller than the diameter of said first core section.

8. The set screw of claim 1 wherein said torque-limiting portion includes a peripheral break notch.

9. The set screw of claim 1 comprising a starter thread in an interior surface of said cylindrical bore to facilitate removal of said set screw.

10. The set screw of claim 1 comprising a reverse thread in an interior surface of said cylindrical bore internal of said lower portion.

11. The set screw of claim 1 wherein said cylindrical bore has a substantially uniform diameter throughout.

12. A spinal implant set screw and removal tool combination comprising;

a set screw including a grippable upper portion, a lower portion breakably connected to said upper portion and having an external thread, and a cylindrical bore formed in said set screw and extending at least partially through said lower portion internal of said external thread; and a removal tool having a proximal end, a distal end, and a shaft therebetween, said distal end adapted to engage said cylindrical bore to facilitate removal of said set screw.

13. The spinal implant set screw and removal tool combination of claim 12, wherein said distal end of the removal tool includes an external thread.

14. The spinal implant set screw and removal tool combination of claim 12, wherein said set screw includes a reverse threaded portion on an interior surface of said cylindrical bore interior to said lower portion and wherein said removal tool is adapted to matingly engage said reverse threaded portion.

* * * * *